United States Patent [19]

Van Scott et al.

[11] 4,035,510

[45] July 12, 1977

[54] TREATMENT OF ACNE UTILIZING N-METHYLDIETHANOLAMINE

[76] Inventors: Eugene J. Van Scott, 1138 Sewell Lane, Rydal, Pa. 19046; Ruey J. Yu, 4400 Dexter St., Philadelphia, Pa. 19128

[21] Appl. No.: 723,326

[22] Filed: Sept. 15, 1976

[51] Int. Cl.$^2$ .................................... A61K 31/13
[52] U.S. Cl. ................................................ 424/325
[58] Field of Search .................................... 424/325

[56] References Cited

U.S. PATENT DOCUMENTS

| | | | |
|---|---|---|---|
| 2,163,099 | 6/1939 | Maxwell | 260/584 R |
| 2,451,942 | 10/1948 | Gresham | 260/584 R |
| 2,541,088 | 2/1951 | Nikawitz | 260/584 R |
| 3,920,840 | 11/1975 | Van Scott et al. | 424/325 |

OTHER PUBLICATIONS

Merck Index, 8th Edition, (1968), p. 356.
Chemical Abstracts vol. 53: 3050(e), (1959).

*Primary Examiner*—Norman A. Drezin
*Attorney, Agent, or Firm*—LeBlanc & Shur

[57] ABSTRACT

Preventive as well as therapeutic treatment of acne vulgaris (hereafter referred to as acne) consisting of the topical application of a solution, lotion or cream containing N-methyldiethanolamine is disclosed. Topical application to uninvolved or involved skin has been found to achieve respectively a complete prevention or a substantial remission of acne.

5 Claims, No Drawings

TREATMENT OF ACNE UTILIZING N-METHYLDIETHANOLAMINE

Acne is a skin disorder which affects most people primarily in the adolescent age range. The principal clinical manifestation of the disease is usually a variety of lesions consisting of comedones, papules, pustules, nodules and cysts. The most frequent site of acne is the face, and to a lesser extent, the back, chest and shoulders.

The basic cause of acne is still unknown. Nevertheless, considerable data on various factors involved in its pathogenesis have been accumulated in recent years. It has been known for some time that acne develops in the pilosebaceous follicle, specifically the formation of follicular plugs (comedones). The normal pilosebaceous follicle includes a follicular canal which is open at one end to the surface of the skin through a follicular orifice and which terminates at its other end in a follicular cul de sac located in the dermal layer of the skin.

Surrounding the neck of the follicular canal are one or more multiacinar holocrine sebaceous glands which empty into the lumen of the follicular canal by means of glandular ducts. The acini of the glands have a peripheral layer of highly proliferating undifferentiated basal cells. As these basal cells are displaced from the periphery to the center of the acini by the proliferation of other basal cells, they mature and differentiate into lipid-producing cells. These cells continue to produce a variety of lipids and to store such lipids in their cytoplasm.

As lipids accumulate in the cells, the cytoplasm appears foamy, the cells enlarge, and the nuclei become distorted and disappear. The cells finally rupture, and the lipids of the cells, along with the cellular debris, form the secretory product known as sebum. In the normal state, the sebum is expelled through the glandular duct into the follicular canal, thence to the skin surface. In acne, the normal function of the pilosebaceous follicle is disrupted by an unexplained accumulation of lipids and keratinous material in the mid-portion of the follicular canal, which accumulation ultimately becomes a comedo.

As more lipids and keratinous materials are deposited onto the comedo, the follicular canal begins to distend. When the comedo is exposed to the surface of the skin, it is classified as "open"; otherwise, it is referred to as "closed." Open comedones generally are not inflammatory while closed comedones may evolve into inflamed pustules, papules, or cysts.

Therapeutic regimens for acne include local and systemic treatments, although the former is necessary in the vast majority of cases to dislodge comedones. Local treatment currently consists mainly of topical application of a variety of chemical agents which variously include sulfur, resorcinol, salicylic acid, benzoyl peroxide, Vleminck's solution (comprised of sulfur, calcium polysulfide, and calcium thiosulfate), and retinoic acid (Vitamin A acid). All the foregoing topical agents are known as "peeling" or "drying" agents which exert their therapeutic effect by causing erythema, irritation and desquamation of the skin followed by loosening and expulsion of the comedones. Oral antibiotics are often administered when microbial infections cause inflammatory papules and pustules. Two commonly used antibiotics are tetracycline and erythromycin.

Since the cause of acne is still unknown it is difficult to prevent the occurrence of acne (prophylactic treatment). Once lesions of acne are developed topical treatment with the foregoing "peeling" or "drying" agents often leads to burning or irritation of the skin. Many acne patients discontinue such treatment simply because they can no longer bear the discomfort from these agents. Although the broad spectrum antibiotics are rather effective in the management of infected acne lesions, long term use of those drugs carries a risk of systemic side effects.

It is therefore imperative to develop an efficaceous, nontoxic, nonallergenic and nonirritating substance for the topical treatment of acne.

We have now discovered that acne may be successfully prevented or treated with N-methyldiethanolamine, which is essentially nontoxic, nonallergenic and nonirritating to both animals and humans. When used as a topical agent the prophylactic as well as therapeutic dose of the compound in solution, lotion or cream may vary from 1 to 20% by weight of the total composition. The preferred concentration is however from 2 to 10% by weight.

It has been established through extensive tests on humans having acne that topical application of the aforementioned composition of the present invention is effective, when applied on a daily basis, in preventing development of acne lesions.

Accordingly, it is the object of this invention to provide a cosmetic composition containing N-methyldiethanolamine, which when topically applied will reliably prevent the development of acne.

It is another object of this invention to provide a medicinal composition containing N-methyldiethanolamine, which when topically applied will substantially alleviate the symptoms of acne.

It is still another object to provide a method for treating acne with a nontoxic solution, lotion or cream of the present invention.

It is still another object to provide a safe and efficient method for treating the symptoms of acne through regular topical application of a medicinal composition which will promote healing within about four weeks.

It is yet another object of this invention to provide a method for formulating a cosmetic as well as medicinal composition in solution, lotion or cream which when topically applied at least daily to the skin prone to lesions of acne will prevent the development of acne or result in a restoration of normal healthy skin condition.

PREPARATION OF THE THERAPEUTIC COMPOSITIONS

N-methyldiethanolamine, also known as methyl bis ($\beta$-hydroxyethyl) amine $CH_3N(CH_2CH_2OH)_2$, M.W.119, b.p. 246°–248° is commercially available as a colorless syrupy substance with a density of 1.038.

To prepare prophylactic as well as therapeutic compositions of this invention, N-methyldiethanolamine is initially dissolved in water. To improve the suitability of the composition for topical use on human skin ethanol and propylene glycol may be added to the aqueous solution. The ratio of each vehicle may vary; however, the preferred concentration of ethanol and propylene glycol should not exceed 70% and 30%, respectively. Generally, the concentration of N-methyldiethanolamine is from 1 to 20% by weight of the total concentration. The preferred concentration range, however, is from 2 to 10%.

The prophylactic or therapeutic composition may also be prepared in forms of lotions, creams or soap bars. In these instances, cosmetically acceptable ingredients are incorporated into the formulation, and lotions, creams or soap bars are readily prepared. The concentration of N-methyldiethanolamine in those compositions is the same as that in the solution form.

The following are illustrative examples of formulations of compositions according to this invention. Although the examples represent only certain types of formulations, in the interest of clarity it should be understood that the following examples are illustrative and not limited.

EXAMPLE 1

N-methyldiethanolamine 5 mls is dissolved in 55 mls of water and the solution admixed with 40 mls of ethanol. This composition consists of 5% active ingredient. The therapeutic solution thus prepared may be stored in brown dropper bottles.

EXAMPLE 2

N-methyldiethanolamine 3 mls is dissolved in 40 mls of water and the solution admixed with 40 mls of ethanol and 20 mls of propylene glycol. The solution thus prepared is stored in brown dropper bottles.

EXAMPLE 3

N-methyldiethanolamine 10 mls is dissolved in 8 mls of water and the solution admixed with 2 mls of 4N HCl. The solution is then admixed with 80 g of water-washable lotion prepared from polyoxyethylene sorbitan mono oleate, cetyl alcohol and water. The ingredients of said water-washable lotion are present in 5:8:87 parts by weight, respectively. The lotion thus prepared is stored in a plastic squeeze bottle having a nozzle attached thereto.

EXAMPLE 4

| Part A: | Polyoxyethylene sorbitan mono oleate | 5 | grams |
|---------|--------------------------------------|-----|-------|
|         | Cetyl alcohol                        | 27  | grams |
|         | Cholesterol                          | 0.4 | gram  |
|         | Squalene                             | 0.2 | gram  |
| Part B: | Water                                | 48  | mls   |
|         | Propylene glycol                     | 10  | mls   |
|         | N-methyldiethanolamine               | 5   | mls   |
|         | 4N HCl                               | 5   | mls   |

Heat Part A to 70° C and heat Part B to 75° C. Add Part B slowly to Part A with agitation. Continue agitation until the mixture is congealed.

TEST RESULTS

A total of 37 patients having moderate to severe papular-pustular acne were selected for this study. Each patient was instructed to apply a test solution, prepared according to Example 1, topically twice daily on the skin of the face for four weeks. Standardized color photos were taken of the full face and/or each side of the face prior to initiating the treatment of the study and after 4 weeks of topical treatment with the test solution. The test results were determined both by clinical impression and also by comparison of the photos before and after treatment. A total of 33 patients showed substantial reduction in the number of acne lesions, or complete resolution of all lesions, after 4 weeks of topical treatment. On continued use, it was also discovered that daily topical application of the above preparation could prevent the development of new acne lesions for periods now extending beyond four months.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced herein.

What is claimed and desired to be secured by U.S. Letters Patent is:

1. A method for treating acne vulgaris in humans having skin affected thereby without irritating the skin comprising:
administering topically to the affected skin a therapeutically effective amount of a composition comprising N-methyldiethanolamine in a pharmacologically acceptable vehicle, on a daily basis to promote improvement of the skin without irritation thereto and to prevent recurrence of acne lesions.

2. The method of claim 1 wherein N-methyldiethanolamine is present in from 1 to 20% by weight of said composition.

3. The method of claim 1 wherein N-methyldiethanolamine is present in 2 to 10% by weight of said composition.

4. The method of claim 1 wherein said vehicle comprises a mixture of water, ethanol and propylene glycol wherein the concentration of ethanol and propylene glycol does not exceed about 70% and 30%, respectively.

5. The method of claim 1 wherein said vehicle is a mixture of water and ethanol wherein the concentration of ethanol does not exceed about 70%.

* * * * *